(12) United States Patent
Habel

(10) Patent No.: US 10,261,058 B2
(45) Date of Patent: Apr. 16, 2019

(54) METHOD AND SYSTEM FOR LIQUID CHROMATOGRAPHY DATA ANALYSIS

(71) Applicant: Bio-Rad Laboratories, Inc., Hercules, CA (US)

(72) Inventor: Jeff Habel, Alameda, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 1025 days.

(21) Appl. No.: 14/592,308

(22) Filed: Jan. 8, 2015

(65) Prior Publication Data

US 2015/0198573 A1 Jul. 16, 2015

Related U.S. Application Data

(60) Provisional application No. 61/927,206, filed on Jan. 14, 2014.

(51) Int. Cl.
| | | |
|---|---|---|
| *G01N 33/48* | (2006.01) | |
| *G01N 33/50* | (2006.01) | |
| *G01N 30/86* | (2006.01) | |
| *G06F 19/18* | (2011.01) | |
| *G01N 30/74* | (2006.01) | |
| *G01N 30/46* | (2006.01) | |

(52) U.S. Cl.
CPC ......... *G01N 30/86* (2013.01); *G01N 30/8631* (2013.01); *G01N 30/8682* (2013.01); *G06F 19/18* (2013.01); *G01N 30/46* (2013.01); *G01N 30/74* (2013.01); *G01N 30/8651* (2013.01); *G01N 30/8658* (2013.01)

(58) Field of Classification Search
None
See application file for complete search history.

(56) References Cited

U.S. PATENT DOCUMENTS

| | | | | |
|---|---|---|---|---|
| 4,631,687 | A  * | 12/1986 | Kowalski | ............... G01N 21/31 702/28 |
| 5,522,988 | A | 6/1996 | Cortes et al. | |
| 6,017,745 | A | 1/2000 | Minkley et al. | |
| 2003/0224354 | A1 | 12/2003 | Gallagher et al. | |
| 2004/0126892 | A1 | 7/2004 | Bogomolov et al. | |
| 2010/0047904 | A1 | 2/2010 | Forde et al. | |
| 2016/0209380 | A1* | 7/2016 | Mishima | ............ G01N 30/8624 |

FOREIGN PATENT DOCUMENTS

| | | |
|---|---|---|
| EP | 1544612 A1 | 6/2005 |
| WO | 2009018307 A2 | 2/2009 |
| WO | 2013035639 A1 | 3/2013 |

OTHER PUBLICATIONS

Rathore, A. S. et al; "Large Scale Demonstration of a Process Analytical Technology Application in Bioprocessing: Use of On-line High Performance Liquid Chromatography for Making Real Time Pooling Decisions for Process Chromatography", Am. Inst. of Chem. Eng. Biotechnol. Prog., 26: 448-457, 2010 (Year: 2010).*
Snyder, L. R. "A rapid Appproach to Selecting the Best Experimental Conditions for High-Speed Liquid Column Chromatography. Part I"; Journal of Chromatographic Science, vol. 10. Apr. 1972, pp. 200-212. (Year: 1972).*
Lou, X. eta al; "Superheated high-temperature size-exclusion chromatography with chloroform as the mobile phase for p-conjugated polymers"; Polym. Chem., 2014, 5, 558 (Year: 2014).*
Sham et al. DNA pooling: a tool for large-scale association studies. Nature Reviews Genetics, vol. 3, pp. 862-871. (Year: 2002).*
The Extended European Search Report from EP Appl. No. 15737791. 2, dated Oct. 12, 2016.
Liu, Yet al. Wortmannin, a Widely Used Phosphoinositide 3-Kinase Inhibitor, also Potently Inhibits Mammalian Poio-iike Kinase. Chemistry and Biology, Jan. 2005, vol. 12, No. 1, pp. 99-107 [online], [retrieved on Mar. 16, 2015]. Retrieved from the Internet <URL:http://ac.els-cdn.com/S 107 4552104003291 /1-s2.0-S1074552104003291-main.pdf?_tid=ded8be9e-cc33-11 e4-a 794-00000aab0f02&acdnat=1426548568_1389820c2c19175769970cd2245fcc05>; p. 104, figure 6.
Search Report, dated Apr. 13, 2015, for International Patent Application PCT/US2015/10760, 3 pages.
Written opinion, dated Apr. 13, 2015, for International Patent Application PCT/US2015/10760, 6 pages.
Office Action from CN Appln. No. 201580000866.5, dated Apr. 19, 2017.

* cited by examiner

*Primary Examiner* — Russell S Negin
(74) *Attorney, Agent, or Firm* — Kilpatrick Townsend and Stockton LLP

(57) ABSTRACT

One embodiment of the invention is directed to a method of analyzing liquid chromatography data. The method comprises collecting, by a data processing system, first volume fractions data from a first liquid chromatography column for a first absorbance wavelength of light λ1 from a first run of a liquid chromatography process on a mixture, wherein the first liquid chromatography column screens for a first characteristic of the mixture. The method further comprising, normalizing a first relative peak area for a first volume of a component of interest in the mixture for the first absorbance wavelength λ1 to obtain a first set of purity quotient values PQ1, collecting second volume fractions data from a second liquid chromatography column for a second absorbance wavelength of light λ2 from a second run of a liquid chromatography process on the mixture, wherein the second liquid chromatography column screens for a second characteristic of the mixture, normalizing a second relative peak area for the second volume of the component of interest in the mixture for the second absorbance wavelength λ2 to obtain a second set of purity quotient values PQ2, storing the values PQ1 and PQ2 in a memory, calculating a difference between values PQ1 and PQ2 for each volume fraction location of the first and second volumes to obtain a first set of purity quotient difference ("PQD") values, displaying in a graphical display the first set of PQD values, and determining which volume fractions to pool together based on the display of the first set of PQD values.

20 Claims, 12 Drawing Sheets

PQD Calculation

| # | Fractions- λ3(280nm) | | | | | | | Fractions- λ4(525nm) | | | | | | | PQ$_{525nm}$ | PQ$_{280nm}$ | PQD | |
|---|---|---|---|---|---|---|---|---|---|---|---|---|---|---|---|---|---|---|
| | Rack/Tube | Tube Location | Start (ml) | End (ml) | Collected Volume (ml) | Area (mAU)*(ml) | Relative Area(%) | # | Rack/Tube | Tube Location | Start (ml) | End (ml) | Collected Volume (ml) | Area (mAU)*(ml) | Relative Area(%) | 525 area/vol | 280 area/vol | Diff 525-280 |
| 1 | A/1 | 1A | 0 | 0.77 | 0.77 | 28.22 | 0.46 | 1 | A/1 | 1A | 0 | 0.77 | 0.77 | 20.11 | 1.55 | 2 | 1 | 1 |
| 2 | A/2 | 2A | 0.77 | 1.52 | 0.75 | 40.40 | 0.65 | 2 | A/2 | 2A | 0.77 | 1.52 | 0.75 | 20.58 | 1.58 | 2 | 1 | 1 |
| 3 | A/3 | 3A | 1.52 | 2.27 | 0.75 | 124.35 | 2.01 | 3 | A/3 | 3A | 1.52 | 2.27 | 0.75 | 32.47 | 2.5 | 3 | 3 | 1 |
| 4 | A/4 | 4A | 2.27 | 3.02 | 0.75 | 242.42 | 3.92 | 4 | A/4 | 4A | 2.27 | 3.02 | 0.75 | 39.01 | 3 | 4 | 5 | -1 |
| 5 | A/5 | 5A | 3.02 | 3.77 | 0.75 | 342.05 | 5.53 | 5 | A/5 | 5A | 3.02 | 3.77 | 0.75 | 45.82 | 3.53 | 5 | 7 | -3 |
| 6 | A/6 | 6A | 3.77 | 4.52 | 0.75 | 281.01 | 4.54 | 6 | A/6 | 6A | 3.77 | 4.52 | 0.75 | 35.11 | 2.7 | 4 | 6 | -2 |
| 7 | A/7 | 7A | 4.52 | 5.01 | 0.48 | 184.44 | 2.98 | 7 | A/7 | 7A | 4.52 | 5.01 | 0.48 | 20.37 | 1.57 | 3 | 6 | -3 |
| 8 | A/8 | 8A | 5.01 | 5.77 | 0.77 | 205.25 | 3.32 | 8 | A/8 | 8A | 5.01 | 5.77 | 0.77 | 28.07 | 2.16 | 3 | 4 | -2 |
| 9 | A/9 | 9A | 5.77 | 6.52 | 0.75 | 172.31 | 2.79 | 9 | A/9 | 9A | 5.77 | 6.52 | 0.75 | 22.9 | 1.76 | 2 | 4 | -1 |
| 10 | A/10 | 10A | 6.52 | 7.27 | 0.75 | 181.17 | 2.93 | 10 | A/10 | 10A | 6.52 | 7.27 | 0.75 | 21.11 | 1.62 | 2 | 4 | -2 |
| 11 | A/11 | 11A | 7.27 | 8.02 | 0.75 | 177.45 | 2.87 | 11 | A/11 | 11A | 7.27 | 8.02 | 0.75 | 18.36 | 1.41 | 2 | 4 | -2 |
| 12 | A/12 | 12A | 8.02 | 8.77 | 0.75 | 147.55 | 2.39 | 12 | A/12 | 12A | 8.02 | 8.77 | 0.75 | 14.85 | 1.14 | 2 | 3 | -2 |
| 13 | A/13 | 12B | 8.77 | 9.52 | 0.75 | 110.89 | 1.79 | 13 | A/13 | 12B | 8.77 | 9.52 | 0.75 | 12.89 | 0.99 | 1 | 2 | -1 |
| 14 | A/14 | 11B | 9.52 | 10.27 | 0.75 | 79.73 | 1.29 | 14 | A/14 | 11B | 9.52 | 10.27 | 0.75 | 11.49 | 0.88 | 1 | 2 | -1 |
| 15 | A/15 | 10B | 10.27 | 11.02 | 0.75 | 54.13 | 0.88 | 15 | A/15 | 10B | 10.27 | 11.02 | 0.75 | 6.98 | 0.54 | 1 | 1 | 0 |
| 16 | A/16 | 9B | 11.02 | 11.77 | 0.75 | 37.83 | 0.61 | 16 | A/16 | 9B | 11.02 | 11.77 | 0.75 | 3.7 | 0.28 | 0 | 1 | 0 |

| | | | | | | 301 | | 302 | | | | | | | 303 | 304 | | 305 | 310 | 315 |
|---|---|---|---|---|---|---|---|---|---|---|---|---|---|---|---|---|---|---|---|---|
| 17 | A/17 | 8B | 11.77 | 12.52 | 0.75 | 28.41 | 0.46 | 17 | A/17 | 8B | 11.77 | 12.52 | 0.75 | 1.65 | 0.13 | — | — | 2 | 0 |
| 18 | A/18 | 7B | 12.52 | 13.27 | 0.75 | 22.28 | 0.36 | 18 | A/18 | 7B | 12.52 | 13.27 | 0.75 | 1.62 | 0.12 | — | — | 0 | 0 |
| 19 | A/19 | 6B | 13.27 | 14.02 | 0.75 | 17.47 | 0.28 | 19 | A/19 | 6B | 13.27 | 14.02 | 0.75 | 1.73 | 0.13 | — | — | 0 | 0 |
| 20 | A/20 | 5B | 14.02 | 14.77 | 0.75 | 14.16 | 0.23 | 20 | A/20 | 5B | 14.02 | 14.77 | 0.75 | 1.99 | 0.15 | — | — | 0 | 0 |
| 21 | A/21 | 4B | 14.77 | 15.01 | 0.23 | 3.82 | 0.06 | 21 | A/21 | 4B | 14.77 | 15.01 | 0.23 | 0.8 | 0.06 | — | — | 0 | 0 |
| 22 | A/22 | 3B | 15.01 | 15.21 | 0.2 | 2.66 | 0.04 | 22 | A/22 | 3B | 15.01 | 15.21 | 0.2 | 0.37 | 0.03 | — | — | 0 | 0 |
| 23 | A/23 | 2B | 15.21 | 15.41 | 0.2 | 2.31 | 0.04 | 23 | A/23 | 2B | 15.21 | 15.41 | 0.2 | 0.29 | 0.02 | — | — | 0 | 0 |
| 24 | A/24 | 1B | 15.41 | 15.61 | 0.2 | 2.17 | 0.04 | 24 | A/24 | 1B | 15.41 | 15.61 | 0.2 | 0.29 | 0.02 | — | — | 0 | 0 |
| 25 | A/25 | 1C | 15.61 | 15.81 | 0.2 | 2.16 | 0.03 | 25 | A/25 | 1C | 15.61 | 15.81 | 0.2 | 0.41 | 0.03 | — | — | 0 | 0 |
| 26 | A/26 | 2C | 15.81 | 16.01 | 0.2 | 1.94 | 0.03 | 26 | A/26 | 2C | 15.81 | 16.01 | 0.2 | 0.49 | 0.04 | — | — | 0 | 0 |
| 27 | A/27 | 3C | 16.01 | 16.21 | 0.2 | 1.68 | 0.03 | 27 | A/27 | 3C | 16.01 | 16.21 | 0.2 | 0.47 | 0.04 | — | — | 0 | 0 |
| 28 | A/28 | 4C | 16.21 | 16.41 | 0.2 | 1.48 | 0.02 | 28 | A/28 | 4C | 16.21 | 16.41 | 0.2 | 0.47 | 0.04 | — | — | 0 | 0 |
| 29 | A/29 | 5C | 16.41 | 16.61 | 0.2 | 1.28 | 0.02 | 29 | A/29 | 5C | 16.41 | 16.61 | 0.2 | 0.46 | 0.04 | — | — | 0 | 0 |
| 30 | A/30 | 6C | 16.61 | 16.81 | 0.2 | 1 | 0.02 | 30 | A/30 | 6C | 16.61 | 16.81 | 0.2 | 0.35 | 0.03 | — | — | 0 | 0 |
| 31 | A/31 | 7C | 16.81 | 17.01 | 0.2 | 0.7 | 0.01 | 31 | A/31 | 7C | 16.81 | 17.01 | 0.2 | 0.15 | 0.01 | — | — | 0 | 0 |
| 32 | A/32 | 8C | 17.01 | 17.21 | 0.2 | 0.68 | 0.01 | 32 | A/32 | 8C | 17.01 | 17.21 | 0.2 | 0.21 | 0.02 | — | — | 0 | 0 |
| 33 | A/33 | 9C | 17.21 | 17.41 | 0.2 | 0.5 | 0.01 | 33 | A/33 | 9C | 17.21 | 17.41 | 0.2 | 0.21 | 0.02 | — | — | 0 | 0 |
| 34 | A/34 | 10C | 17.41 | 17.61 | 0.2 | 0.39 | 0.01 | 34 | A/34 | 10C | 17.41 | 17.61 | 0.2 | 0.19 | 0.01 | — | — | 0 | 0 |
| 35 | A/35 | 11C | 17.61 | 17.81 | 0.2 | 0.14 | 0 | 35 | A/35 | 11C | 17.61 | 17.81 | 0.2 | 0.15 | 0.01 | — | — | 0 | 0 |
| 36 | A/36 | 12C | 17.81 | 18.01 | 0.2 | 0.08 | 0 | 36 | A/36 | 12C | 17.81 | 18.01 | 0.2 | 0.12 | 0.01 | — | — | 0 | 0 |

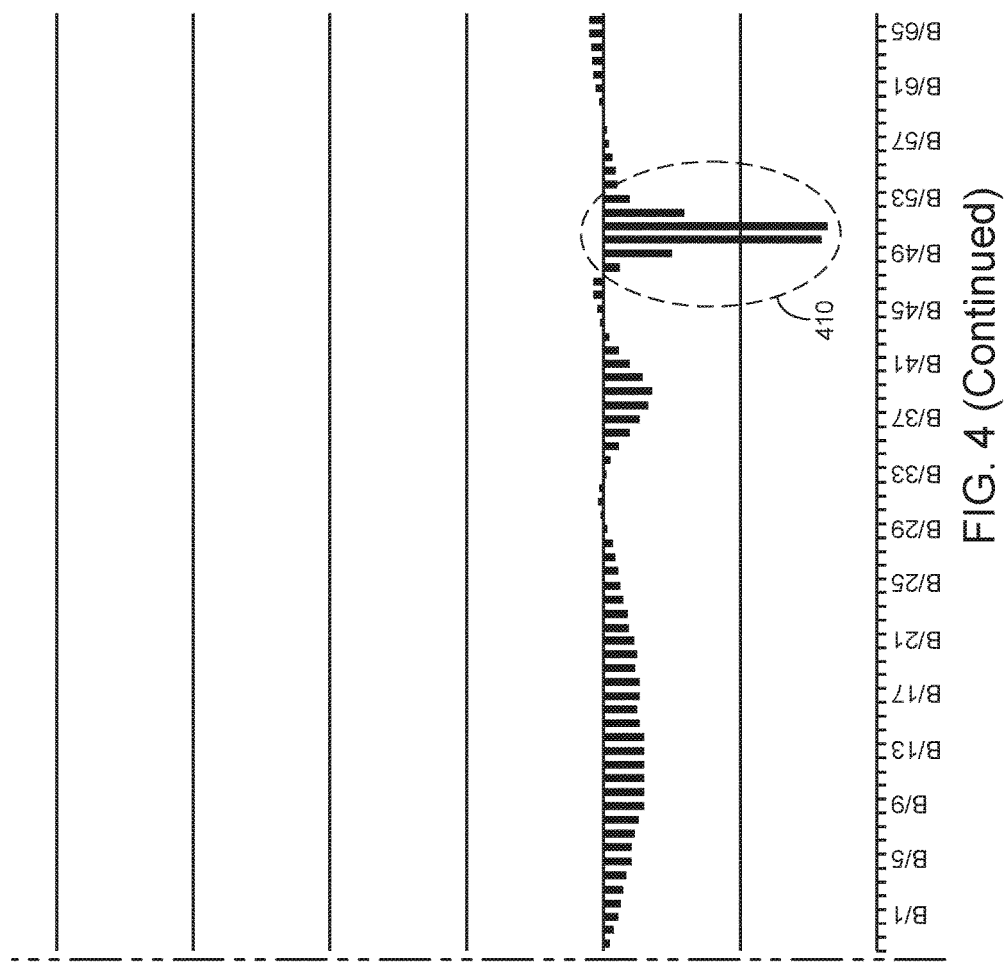

METHOD AND SYSTEM FOR LIQUID CHROMATOGRAPHY DATA ANALYSIS

CROSS-REFERENCES TO RELATED APPLICATIONS

This application is a nonprovisional of and claims the benefit of priority of U.S. Provisional Application No. 61/927,206, titled, "Method and System for Liquid Chromatography Data Analysis," filed on Jan. 14, 2014, which is herein incorporated by reference in its entirety for all purposes.

BACKGROUND OF THE INVENTION

Liquid chromatography is a chromatographic technique used to separate components of a mixture based on a particular characteristic of the components. Liquid chromatography is used to identify each component in a mixture and to quantify each component. In general, liquid chromatography involves a liquid sample being passed over a solid adsorbent material packed into a column using a flow of liquid solvent. Each component (e.g., analyte) in the sample interacts slightly differently with the adsorbent material, thus retarding the flow of the analytes. If the interaction is weak, the analytes flow off the column in a short amount of time, and if the interaction is strong, then the analytes take a longer time to flow off the column.

The active component of the column, referred to as the sorbent, is typically a granular material made of solid particles (e.g., silica, polymers, etc.), and can range from approximately 2-50 micrometers in size. The components of the sample mixture are separated from each other due to their different degrees of interaction with the sorbent particles. The pressurized liquid is typically a mixture of solvents (e.g. water, acetonitrile or methanol) and is referred to as a "mobile phase". The composition and temperature of the mobile phase liquid plays a major role in the separation process by influencing the interactions between sample components and the sorbent. These interactions are physical in nature, such as hydrophobic (dispersive), dipole-dipole and ionic, or some combination thereof.

The sample mixture to be separated and analyzed is introduced, in a discrete small volume (typically microliters), into the stream of mobile phase percolating through the column. The components of the sample move through the column at different velocities, which are function of specific physical interactions with the sorbent (also called stationary phase). The velocity of each component depends on its chemical nature, on the nature of the stationary phase (column) and on the composition of the mobile phase. The time at which a specific analyte emerges from the column is referred to as its "retention time". The retention time measured under particular conditions is considered an identifying characteristic of a given analyte.

A liquid chromatography system generally includes a sampler, pumps, and a detector. The sampler brings the sample mixture into the mobile phase stream which carries it into the column. The pumps deliver the desired flow and composition of the mobile phase liquid through the column. The detector generates a signal proportional to the amount of sample component emerging out of the column, thus allowing for quantitative analysis of the sample components. A general-purpose or special purpose digital computer can be configured to control the liquid chromatography system and to provide the data analysis. Various detectors in common use include UV detectors, photodiode arrays ("PDAs"), florescence detectors, or mass spectrometry-based detectors. External detectors may also be used (e.g., fluorescence, refractive index, etc.). Also many different types of columns are available, filled with sorbents varying in particle size.

FIG. 1 depicts an example graphical representation of a liquid chromatography system according to the prior art. In the illustrated embodiment, liquid chromatography unit 100 includes (1) solvent reservoirs, (2) solvent degasser, (3) gradient valve, (4) mixing vessel for delivery of the mobile phase, (5) high-pressure pump, (6) switching valve, (7) sample injection loop, (8) pre-column (guard column), (9) analytical column, (10) detector (e.g., IR or UV), (11) data processing apparatus, and (12) waste collector.

BRIEF SUMMARY OF THE INVENTION

Embodiments described herein relate generally to liquid chromatography analysis. More particularly, the embodiments described herein relate generally to techniques for analyzing liquid chromatography data to optimize separation of one or more components of interest from impurities in a mixture.

For example, one embodiment of the invention is directed to a method of analyzing liquid chromatography data. The method comprises collecting, by a data processing system, first volume fractions data from a first liquid chromatography column for a first absorbance wavelength of light $\lambda 1$ from a first run of a liquid chromatography process on a mixture, wherein the first liquid chromatography column screens for a first characteristic of the mixture. The method further comprising, normalizing a first relative peak area for a first volume of a component of interest in the mixture for the first absorbance wavelength $\lambda 1$ to obtain a first set of purity quotient values PQ1, collecting second volume fractions data from a second liquid chromatography column for a second absorbance wavelength of light $\lambda 2$ from a second run of a liquid chromatography process on the mixture, wherein the second liquid chromatography column screens for a second characteristic of the mixture, normalizing a second relative peak area for the second volume of the component of interest in the mixture for the second absorbance wavelength $\lambda 2$ to obtain a second set of purity quotient values PQ2, storing the values PQ1 and PQ2 in a memory, calculating a difference between values PQ1 and PQ2 for each volume fraction location of the first and second volumes to obtain a first set of purity quotient difference ("PQD") values, displaying in a graphical display the first set of PQD values, and determining which volume fractions to pool together based on the display of the first set of PQD values.

Other embodiments of the invention are directed to methods, systems, and computer apparatuses described in further detail herein.

BRIEF DESCRIPTION OF THE DRAWINGS

FIG. 3 depicts a table showing an example purity quotient difference calculation for a liquid chromatography process conducted at two different absorption wavelengths according to one embodiment;

DETAILED DESCRIPTION OF THE INVENTION

Throughout this description for the purposes of explanation, numerous specific details are set forth in order to provide a thorough understanding of the present invention. It will be apparent, however, to one skilled in the art that the present invention may be practiced without some of these specific details. In other instances, well-known structures and devices are shown in block diagram form to avoid obscuring the underlying principles of the described embodiments.

Figure 1:
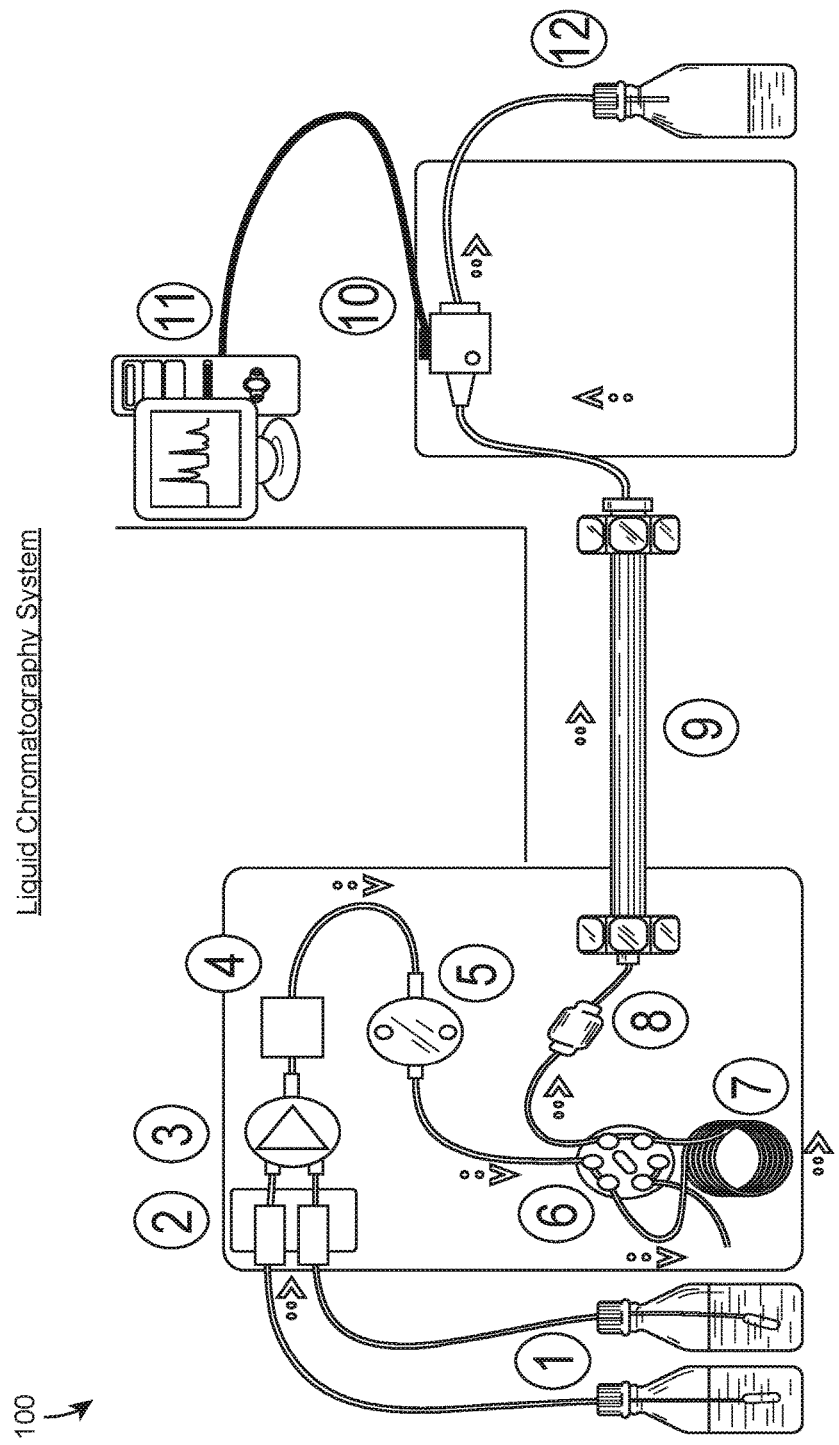
FIG. 1 depicts an example graphical representation of a liquid chromatography system according to the prior art.
Figure 2:
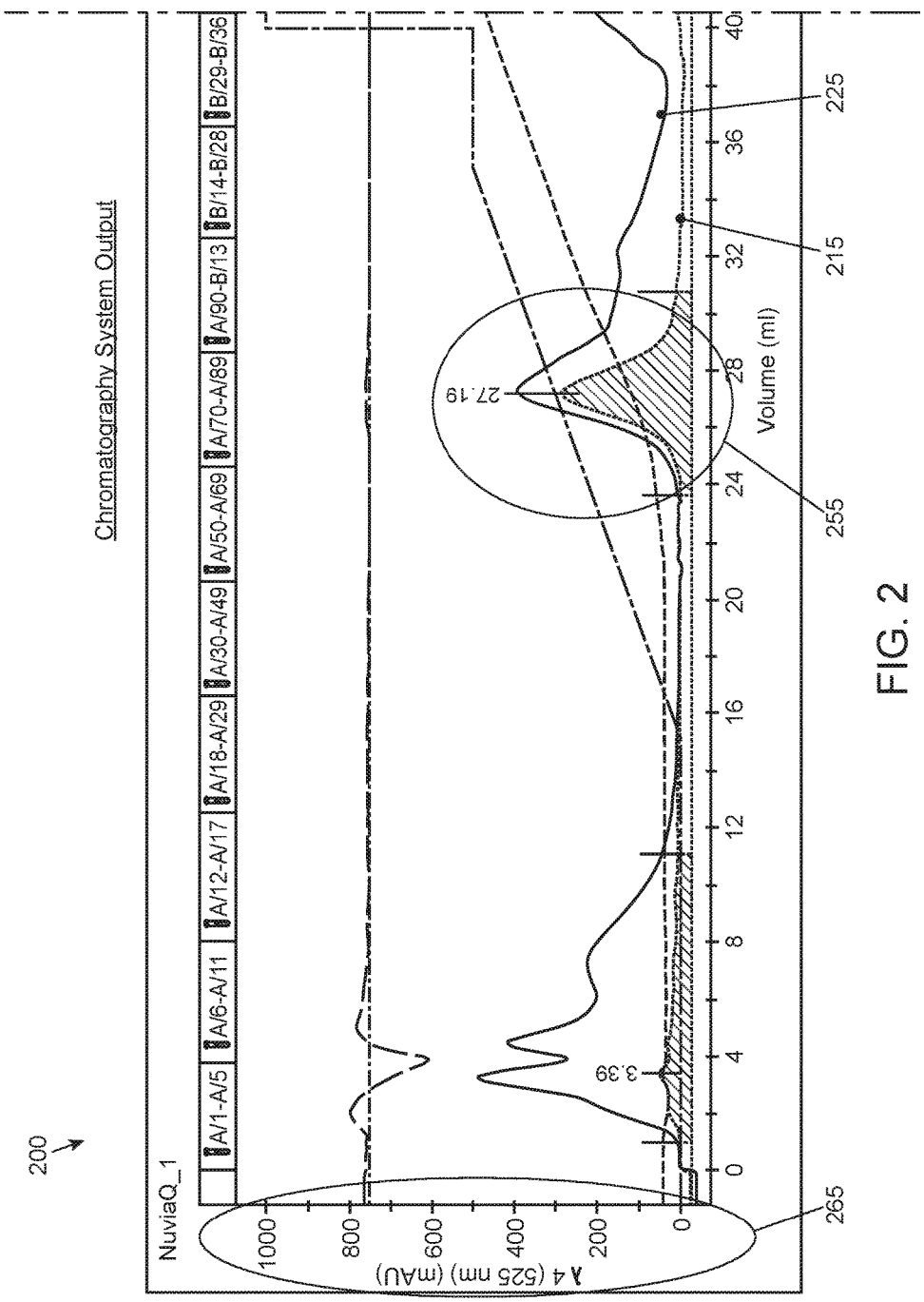
FIG. 2 depicts an example graphical display of an output of a liquid chromatography process conducted at two different absorption wavelengths according to one embodiment.
Figure 2:
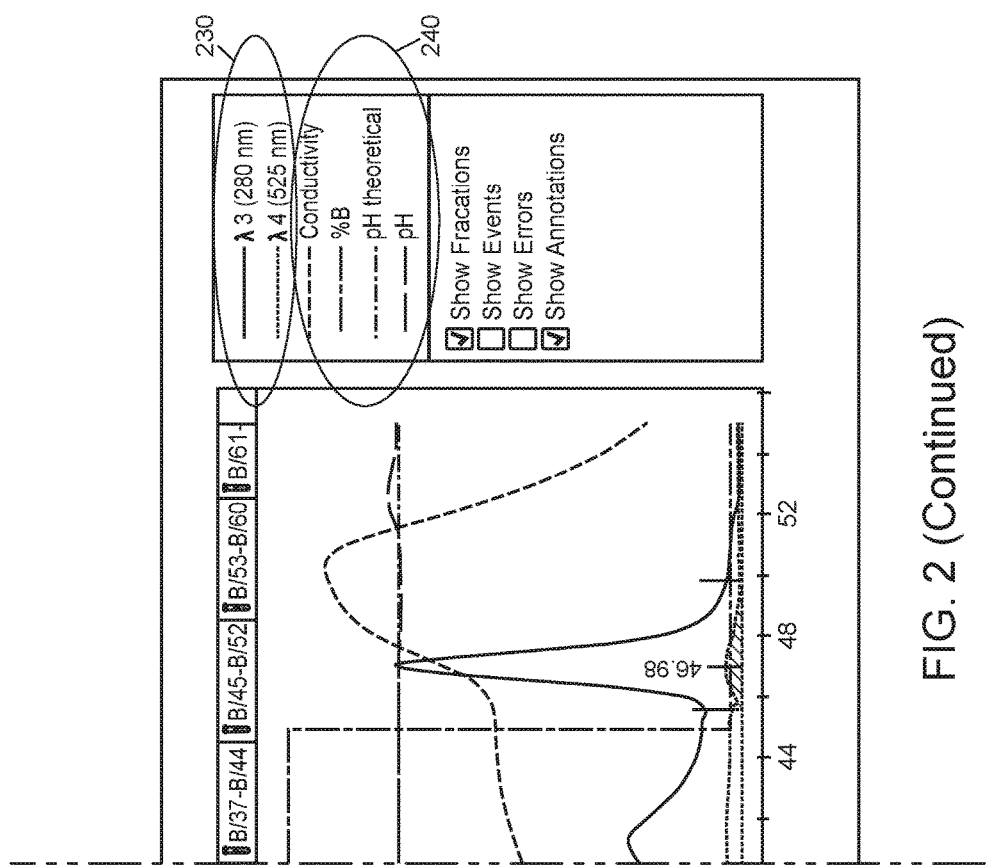

FIG. 2 depicts an example graphical display of an output of a liquid chromatography process conducted at two different absorption wavelengths according to one embodiment. The illustrated embodiment depicts an example output display 200 of a liquid chromatography system such as the data processing apparatus 11 depicted in FIG. 1. In the figure, a liquid chromatography column was used and volume fractions data has been collected therefrom during a run of a liquid chromatography process using this column for two different absorbance wavelengths of light 230. In this particular example, absorbance wavelengths λ3 at 280 nanometers (nm) and wavelength λ4 and 525 nm have been used for the run. As used herein, a "volume fraction" is defined as the volume of a component of interest in a mixture divided by the volume of all components in the mixture. While "fractions" can be defined by the amount collected in various receptacles as output of the chromatograph, the "fractions" (e.g., of time of run or volume output) can also be designated arbitrarily or based on other criteria. That is, for the purposes of the techniques described herein, a "fraction" can be any arbitrary or variable volume of liquid that can be used to calculate a relative area of absorbance. Fractions can be of the same or different sizes as desired. The SI-unit is $m^3/m^3$.

In FIG. 2, a plot of the absorbance wavelength λ3 is shown by line 225 and a plot of the absorbance wavelength λ4 is shown by line 215. The volume fractions data can then be processed by a liquid chromatography system and output onto display 200. The display 200 shows the plot of the volume fractions data for each of the absorbance wavelengths 230. Specifically, display 200 shows a plot of the amount of light absorbed by the mixture at the two absorbance wavelengths 230 for each volume fraction of the column. The y-axis 265 of the plot represents how much light was absorbed by the particular absorbance wavelength and the x-axis of the plot represents the volume fraction locations in milliliters. Display 200 further shows plots of the variables 240 used in this particular run of the liquid chromatography process.

In the illustration, various peaks of the absorbance wavelengths λ3 and λ4 are shown indicating when components of the mixture have flowed off the column at the various volume fractions. For instance, components that absorb light at λ3 exhibit peaks at 3.39 ml, 27.19 ml, and 46.98, and components that absorb light at λ4 exhibit a peak at 27.91. As can be seen, wavelengths λ3 and λ4 have peaks that coincide at 27.19 ml, which is shown by reference designator 225 in the figure. At volumes approximately between 24 ml and 30 ml in the column, the highest concentration of a component of interest flows off of the column.

Systems and methods disclosed herein are adapted to analyze this data output from a liquid chromatography system to assist in determining which set of conditions and variables to apply to the process for optimal results. Specifically, the systems and methods disclosed herein are adapted to analyze liquid chromatography data to assist in determining which volume fractions to pool together for optimal separation of the component of interest from impurities in the mixture. This can be accomplished by performing two or more runs of a liquid chromatography process while changing one variable between each run to determine which run provided more favorable results.

The methods and systems are also adapted to compare two sets of purity quotients ("PQ") values. A PQ value can be determined for some or each volume fraction of a liquid chromatography volume by normalizing the relative peak area for an absorbance wavelength as given by the following equation:

$$PQ_\lambda = \frac{\text{Relative Area } (\%)_\lambda}{\text{Collected Volume } (mL)_\lambda}$$

In one embodiment, normalization occurs by first defining a "fraction" (e.g., volume, time, etc.) and integrating the absorbance under the curve for that fraction size. The resulting integration value is then divided by the size of the fraction to normalize. This can be done for each absorbance wavelength. For instance, referring to FIG. 2, a set of PQ values can be determined for λ3 and a set of PQ values can be determined for λ4.

The set of PQ values therefore represents the resulting normalized curve that indicates the relative area of the component of interest in the mixture as a percentage divided by the total collected volume of the component for each volume fraction location.

Different PQ values can be determined and compared as desired. The difference between the set of PQ values can be calculated at each volume fraction location to obtain a first set of purity quotient difference ("PQD") values as shown by the following equation:

$$PQD = PQ_{\lambda,1} - PQ_{\lambda,2}$$

In one aspect, two different wavelengths or other attributes or variables can be monitored during a run of the liquid chromatography process on a mixture. As shown by the equation above, absorbance at a first wavelength λ1 and a second wavelength λ2 can be monitored with a separate PQ value determined for each (PQλ1 and PQλ2). In some aspects, light being absorbed at a particular wavelength indicates the presence of a target molecule in the mixture.

For example, a target protein may absorb at a particular wavelength at which other proteins do not absorb.

In these aspects, a second wavelength λ2 can absorb light at a fraction representing an attribute shared by the target molecule (which absorbs at for example) and one or more other components of the mixture. For example, wavelength λ2 could be 280 nm, a wavelength at which nearly all proteins absorb. Alternatively, wavelength λ2 can represent a component that is not desired (e.g., a component of the mixture to be excluded). In embodiments where DNA is a contaminant and not desired, the wavelength λ2 could be a wavelength at which DNA (or nucleic acids) absorbs, e.g., 255 nm. In either of the above-described alternatives, maximum PQD (i.e., PQλ1-PQλ2) values can be determined which indicate those fractions having the highest proportion of target component, while having the least amount of undesired components (e.g., non-target proteins or contaminant DNA).

In other aspects, both PQ1 and PQ2 can be used to determine desired components. For example, in cases where one desires to purify protein binding DNA, wavelength λ1 can be the wavelength that the protein absorbs at (e.g., 280 nm) and wavelength λ2 can be the wavelength that DNA or nucleic acids absorb at (e.g., 255 nm). In these aspects, the PQD values indicate where the most overlap of DNA and protein occur in fractions.

In other aspects, the PQ1 and PQ2 values can be used to compare different chromatography runs on the same column or between different columns. In these cases, two runs of the liquid chromatography process can be run at two different times with the same set of variables. Comparison of different runs on the same column can be used to monitor column performance over time and can be used to indicate when the column has become degraded (e.g., when the obtained PQD values significantly differ from a baseline set of PQD values).

In embodiments where different columns are compared (e.g., generating a PQ1 from column 1 and a PQ2 from column 2), the second run of the liquid chromatography process can be used to screen for a different characteristic(s) by varying one or more variables from those used in the first run. This can allow for comparison of relative binding capacities or other chromatography attributes between columns.

In at least certain embodiments, the first and second set of PQD values for the first and second runs of the liquid chromatography process can be displayed in a graphical display superimposed on each other at each of the volume fraction locations. This information can then be used to visually and quantifiably determine which set of the first or second set of PQD values provides a more favorable separation of the component of interest from impurities (or other components) in the mixture.

FIG. 3 depicts a table showing example data for a PQD calculation for a liquid chromatography process conducted at two different absorption wavelengths (λ3 and λ4) according to one embodiment. In the illustrated embodiment, table 300 includes columns 301 and 303 for the total collected volume of the component of interest for each fraction location for the λ3 and λ4 wavelengths respectively, and includes columns 302 and 304 for the relative area of the component of interest in the mixture as a percentage for each fraction location for the λ3 and λ4 wavelengths respectively. Column 305 shows the set of PQ values for λ4 and column 310 shows the set of PQ values for λ3 for each fraction location.

The difference between these sets of PQ values for wavelengths λ4 and λ3 can then be calculated to obtain a set of PQD values for this particular run of the liquid chromatography process. The PQD values are shown in column 315 of table 300. If the component of interest is known to absorb light at wavelength λ3, then the volume fractions where the component will flow off the column can be found by subtracting λ4 from λ3; and if the component of interest is instead known to absorb light at wavelength λ4, then the volume fractions where the component will flow off the column can be found by subtracting λ3 from λ4. PQD values greater than zero indicate there is more of the component of interest in the mixture than impurities for each volume fraction location and PQD values less than zero indicate there is more impurities in the mixture than the component of interest. PQD values equal to zero indicate equal amounts of impurities and of the component of interest in the mixture at each volume fraction location. As can be seen from table 300, the set of PQD values varies between 1 and −3.

Figure 4:
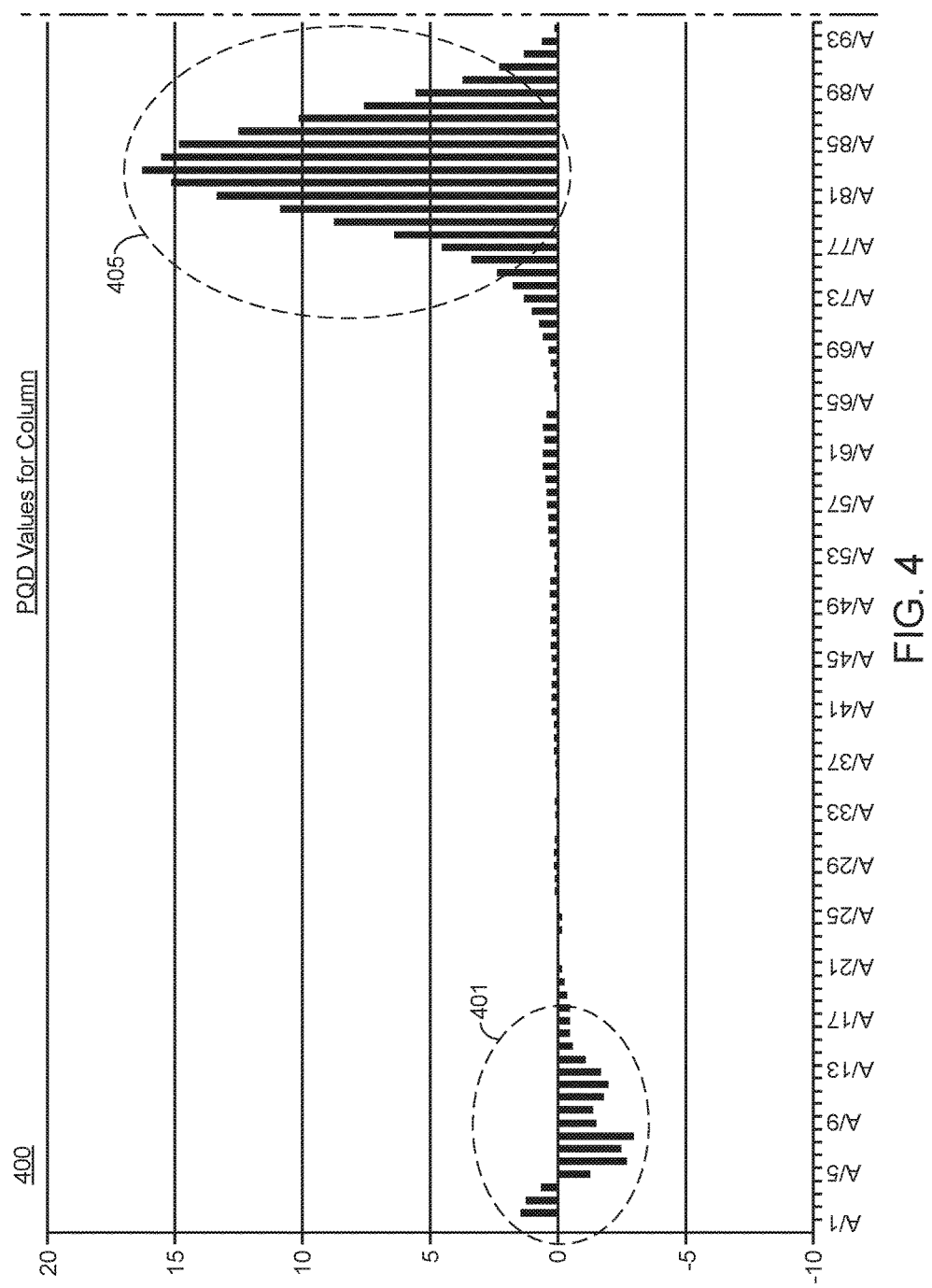
FIG. 4 depicts an example plot of a set of purity quotient difference values for a liquid chromatography process at two different absorption wavelengths according to one embodiment.

The set of PQD values for the column from table 300 is graphically displayed in FIG. 4, which depicts an example plot of a set of PQD values for a liquid chromatography process at two different absorption wavelengths according to one embodiment. In the illustrated embodiment, plot 400 includes a peak at reference designator 405, which represents a peak that occurred approximately between volume fraction locations A/73 and A/89. This is where the highest concentration of the component of interest flows off the column. Plot 400 also includes nulls at reference designators 401 and 410. These volume fraction locations are where the highest concentration of impurities flows off the column.

Figure 5:
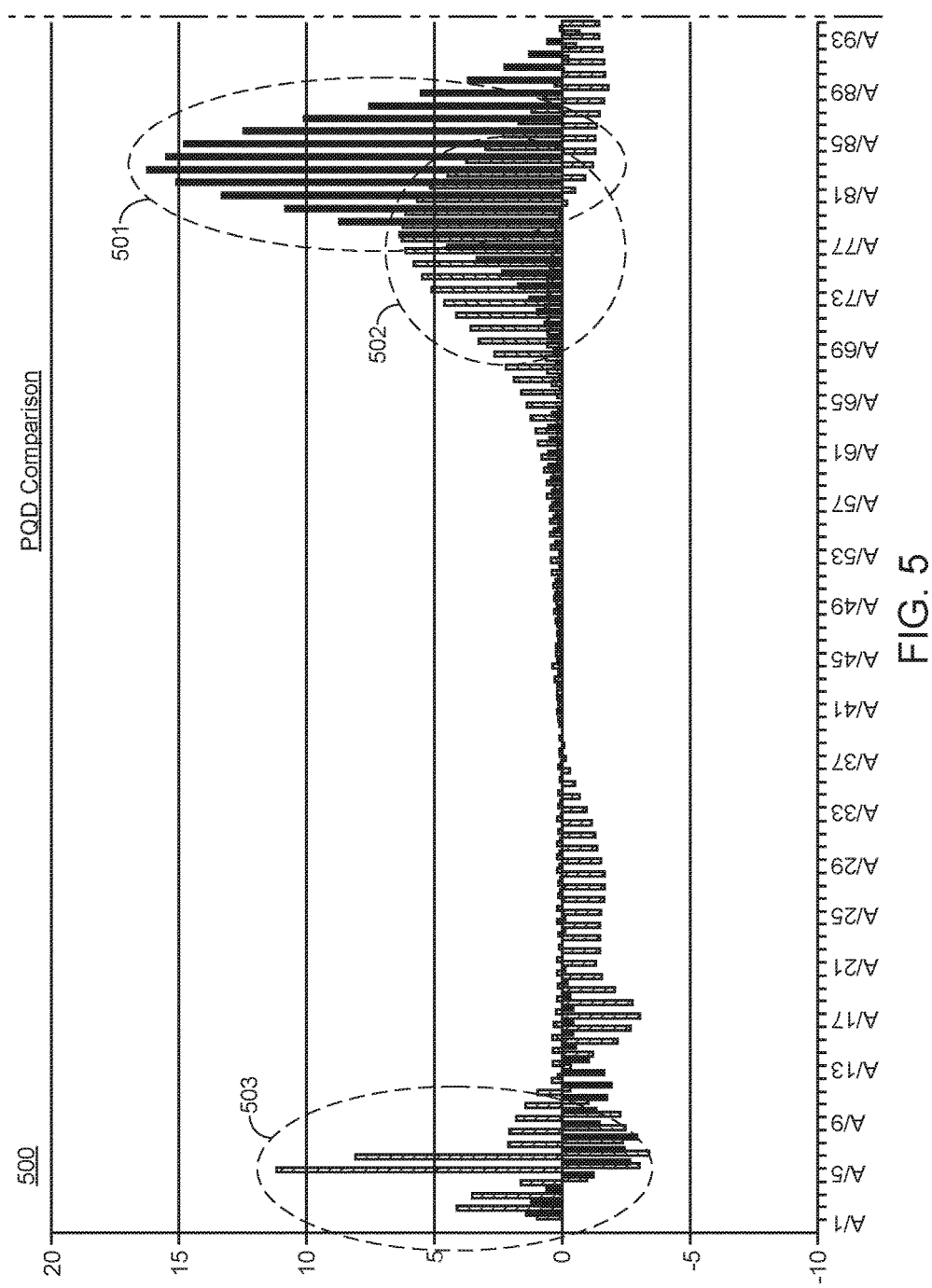
FIG. 5 depicts an example plot of a three sets of purity quotient difference values superimposed on each other for three separate runs of a liquid chromatography process at two different absorption wavelengths according to one embodiment.
Figure 5:
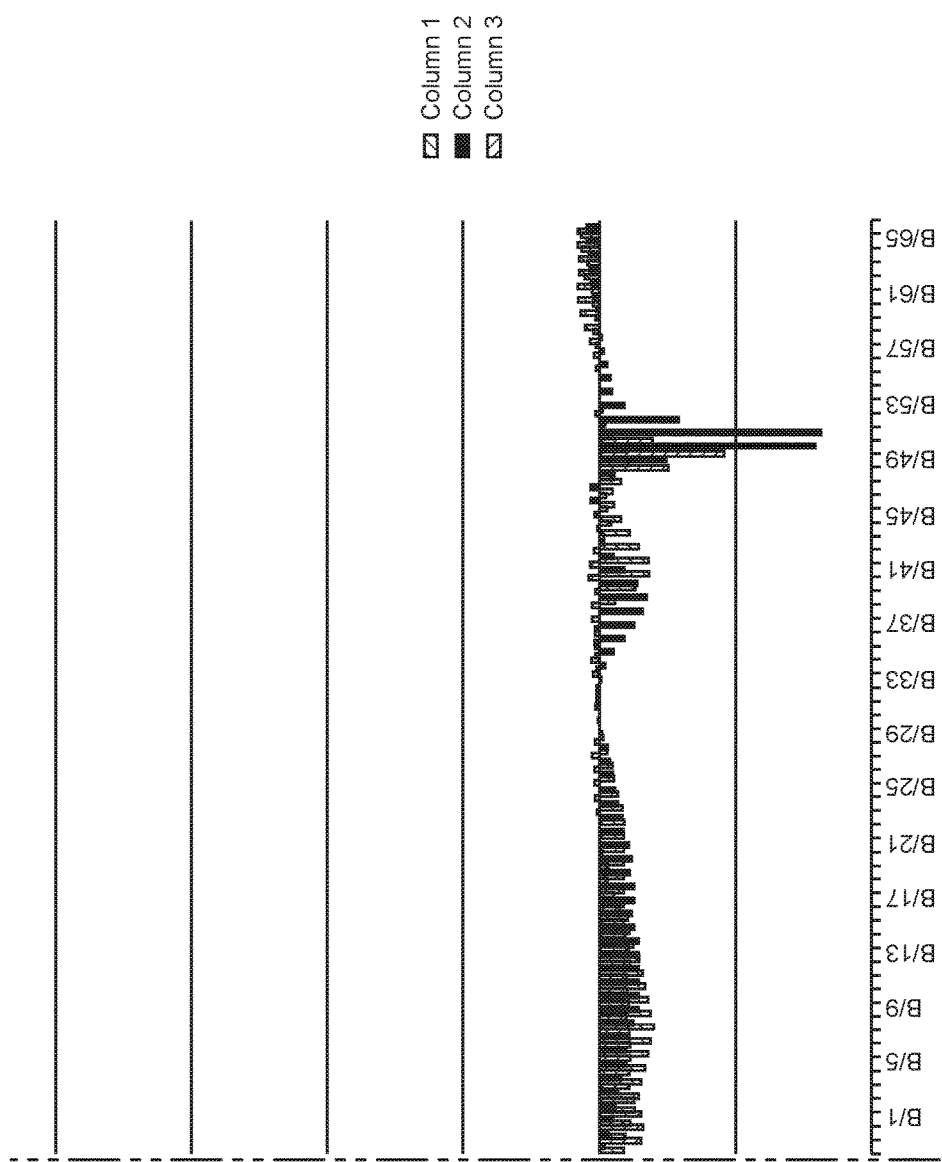

As discussed above, sets of PQD values from different runs of the liquid chromatography process with different columns (or different variables) can be used to visually and quantifiably determine which set of conditions provides a more favorable separation of the component of interest from impurities in the mixture. FIG. 5 depicts an example plot of three sets of purity quotient difference values superimposed on each other for three separate runs of a liquid chromatography process at two different absorption wavelengths according to one embodiment. The set of PQD values shown in plot 500 represent a chromatography run for three different columns (or the same column with three different sets of variables).

The set of PQD values calculated for these runs is displayed superimposed on each other at each of the volume fraction locations. The peaks at reference designators 501 (corresponding to the column 2 run) and 502 (corresponding to the column 1 run) provide the highest concentration of the component of interest as compared to impurities. The peak at reference designator 503 indicates the component of interest flowed out of column 3 too fast, and therefore, did not bind to the substrate. Therefore, column 2 in this example provided the best outcome. Column 1 also provided a good outcome, but the results from the run on column 3 should be ignored.

Figure 6A:
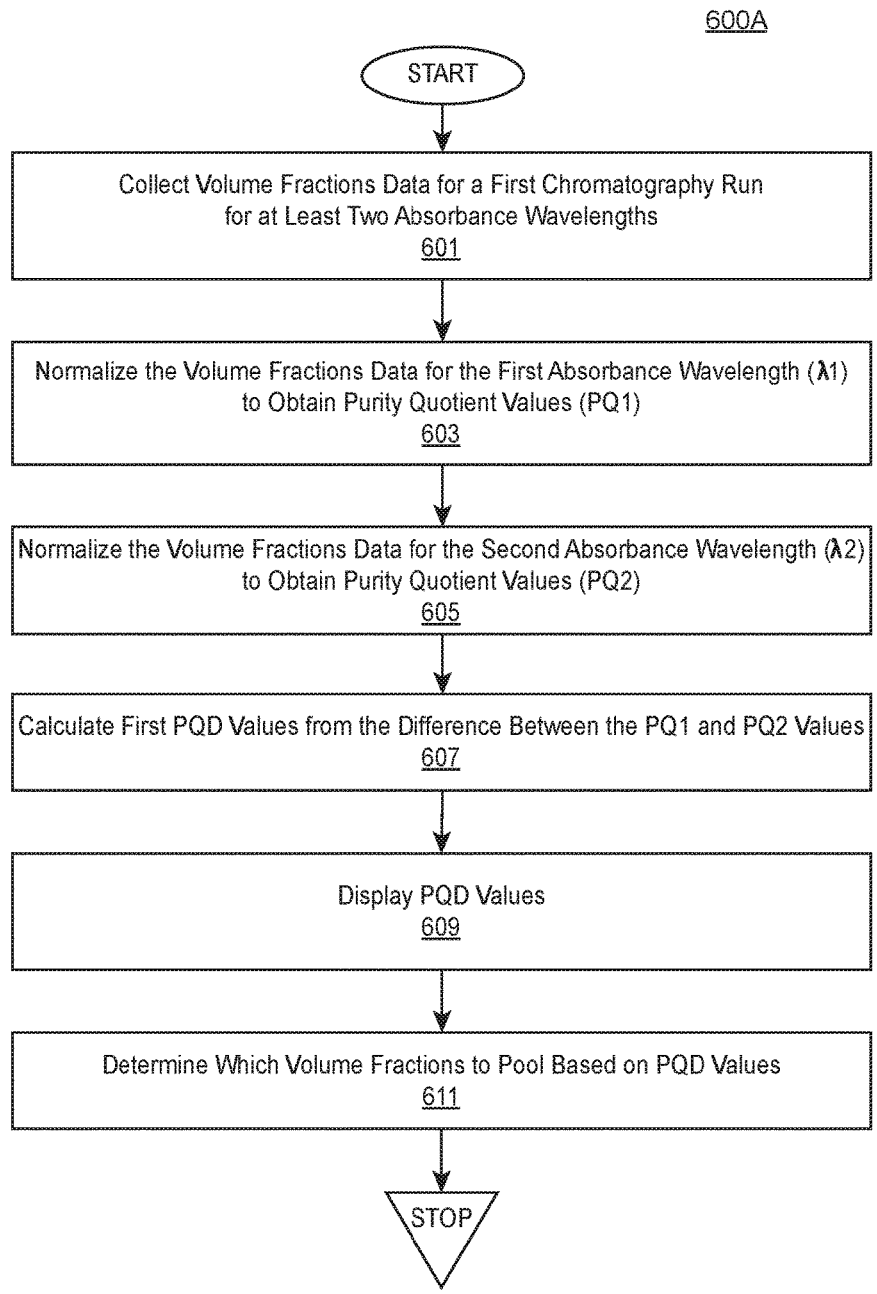
FIG. 6A depicts an example flow chart of a process for analyzing liquid chromatography data according to one embodiment.

FIG. 6A depicts an example flow chart of a process for analyzing liquid chromatography data according to one embodiment. In the illustrated embodiment, process 600A begins at operation 601 where volume fractions data is collected from a liquid chromatography column for at least two absorbance wavelengths of light from a first run of a liquid chromatography process on a mixture. The liquid chromatography column is adapted to screen for a first characteristic of the mixture. In one embodiment, the process includes collecting the chromatography data by performing a liquid chromatography run on a mixture to generate the data; in other embodiments, the chromatography data is provided from other sources.

Process 600A continues at operation 603 where the relative peak area for the first volume of the component of interest in the mixture for the first absorbance wavelengths (λ1) is normalized to obtain a first set of purity quotient ("PQ") values PQ1. In one embodiment, the set of PQ values can be normalized for a volume by dividing the first relative peak area of the component of interest by the total collected volume of the component in the mixture at each volume fraction location of the first volume. At operation 605, the second relative peak area for the first volume of the component of interest in the mixture is also normalized for the second absorbance wavelength (λ2) to obtain a second set of purity quotient values PQ2.

The difference between values PQ1 and PQ2 is calculated for each volume fraction location of the first and second volumes to obtain a first set of purity quotient difference ("PQD") values for the first run of the liquid chromatography process at operation 607, which are displayed in a graphical display at operation 609. For the purposes of this disclosure, any type of graphical display can be used as is well known in the art. From this information, it can then be determined which volume fractions to pool together based on the display of the first set of PQD values (operation 611). This completes process 600A according to one example embodiment.

Figure 6B:
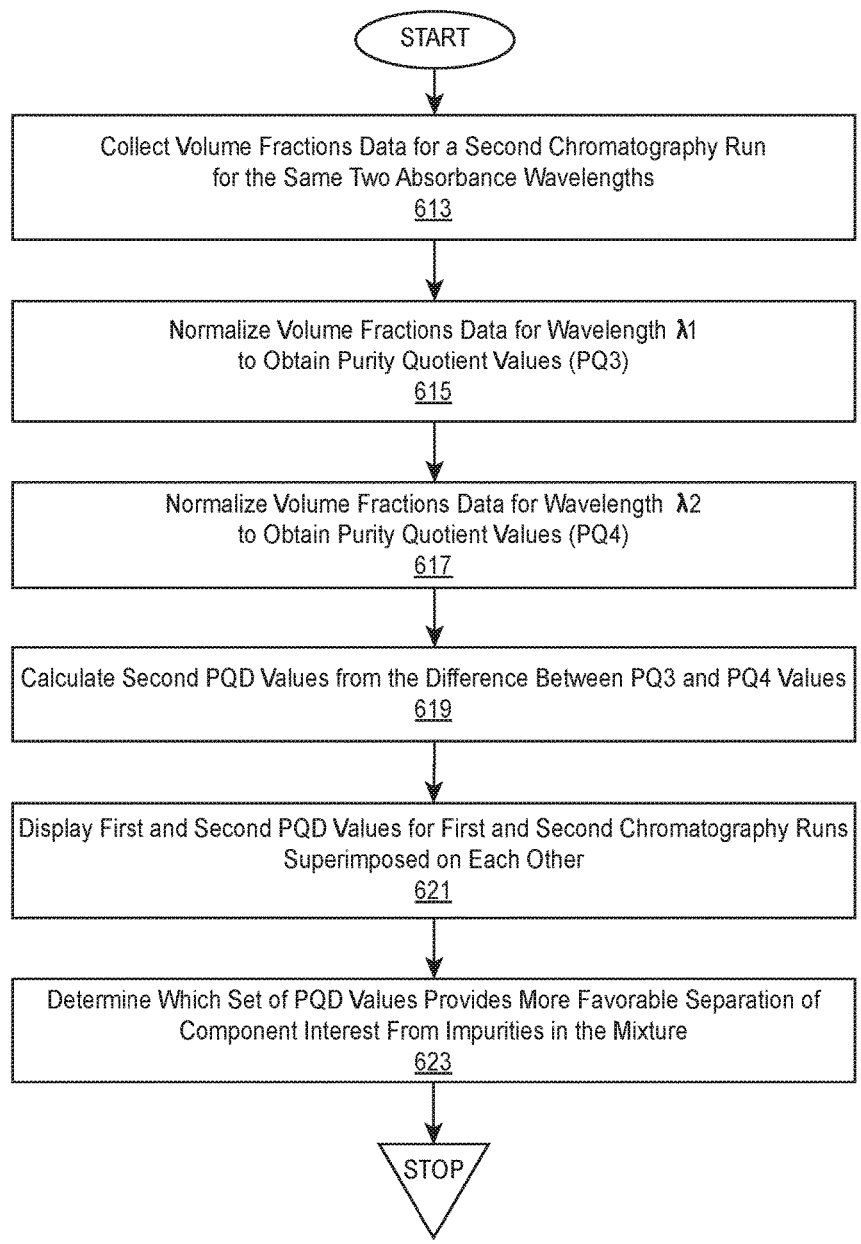
FIG. 6B depicts an example flow chart of a further process for analyzing liquid chromatography data according to one embodiment.

FIG. 6B depicts an example flow chart of a further process for analyzing liquid chromatography data according to one embodiment. In the illustrated embodiment, process 600B begins at operation 613 where volume fractions data from a liquid chromatography column is collected for the two absorbance wavelengths from a second run of the liquid chromatography process on the mixture. This liquid chromatography process is adapted for a second characteristic of the mixture. One or more variables of the liquid chromatography process are varied in the second run. In at least certain embodiments, modifying one of the variables for each subsequent run can be used to determine the best set of conditions (i.e., which variables to use) to obtain optimum separation of the component of interest from impurities in the mixture.

Process 600B continues at operation 615 where the relative peak area for a second volume of the component of interest in the mixture is normalized for the first absorbance wavelength λ1 to obtain a third set of purity quotient values PQ3. And at operation 617, the relative peak area for the second volume of the component of interest in the mixture is normalized for the second absorbance wavelength λ2 to obtain a fourth set of purity quotient values PQ4. The difference between PQ3 and PQ4 is calculated for each volume fraction location to obtain a second set of PQD values (operation 619). The first and second sets of PQD values for the first and second runs of the liquid chromatography process are then displayed superimposed on each other for each volume fraction location at operation 621. In one embodiment, a two-dimensional representation of the first and second sets of PQD values can be displayed based on the first and second runs of the liquid chromatography process on the mixture.

This information can then be used to determine which of the first or second sets of PQD values provides a more favorable separation of the component of interest from impurities in the mixture based on the first and second sets of PQD values (operation 623). Multiple runs of the liquid chromatography process can be performed to further refine the analysis to determine which set of conditions provide the best results. The results of multiple runs can be compared to determine how to optimally set one or more variables of the process. In particular, multiple runs can be performed where one or more variables of the liquid chromatography process can be varied to determine which variables, as well as which values of those variables, can be used in the liquid chromatography process to provide optimal separation of the component of interest from the mixture. Examples of some of the types of variables that can be varied include column type, pH of the mobile phase liquid, conductivity of the mobile phase liquid, and flow rate of the mobile phase liquid.

For instance, three or more runs of the liquid chromatography process can be performed on the mixture where one variable is modified for each additional run. The PQD values can then be displayed in three or more dimensions based on the three or more runs of the liquid chromatography process respectively. Further, in alternate embodiments, PQ values for the component of interest can be subtracted from PQ values of other components in the mixture to identify volume fractions where the highest concentration of the component of interest can be excluded.

In general, the liquid chromatography process can be applied to any absorbance wavelength that can be measured by a spectrophotometric detector. In at least certain embodiments, the relative area values can be obtained from a detector that is external to the liquid chromatography system (e.g., fluorescence, refractive index, etc.). In addition, the peak relative area for the volume of the component of interest in the mixture can be normalized in different ways to produce the same results. For instance, the peak relative area for a can be normalized with respect to: the total volume of the component of interest in the mixture; the volume of the column in the liquid chromatography process; or with respect to time. Other embodiments are possible. This completes process 600 according to one example embodiment.

It should be appreciated that the specific operations illustrated in FIGS. 6A and 6B provide a particular process for analyzing liquid chromatography data according to one embodiment. Other sequences of operations may also be performed according to alternative embodiments. For example, alternative embodiments may perform the operations outlined above in a different order and additional operations may be added or removed depending on the particular applications. Moreover, the individual operations may include one or more sub-operations that may be performed in various sequences as appropriate.

The following list summarizes some potential commercial applications for the data analysis techniques described herein:

(1) In cases where the protein of interest absorbs at an additional wavelength other than about 280 nm, the protein of interest can be separated out from other protein impurities by subtracting the PQ values at about 280 nm from the PQ values at the additional wavelength;

(2) In cases where DNA is a contaminant, the PQ values at about 255 nm (where there is more DNA contaminant than protein) can be subtracted from the PQ values of the protein of interest at 280 nm;

(3) In cases where the protein of interest binds DNA (and therefore DNA would not be a contaminant), PQ values at about 280 nm can be subtracted from the PQ values at about 255 nm to identify where there is the most overlap of DNA and protein;

(4) In cases where the performance of a particular column over time is of interest, the absorbance at about 280 nm from the first run of the liquid chromatography process in the column can be used as a baseline of performance ("PQ1") and the performance of the column after "N" number of runs can be monitored to determine its performance (e.g., does it need to be recharged with ligand, etc.) by subtracting the PQ1 values from the PQ values at the Nth run. In such a case, negative PQ values indicate diminished performance; for example, one can compare a single wavelength from run number 10 against the wavelength from run number 1 for a column performance test (e.g., is the column deteriorating over time with use?). This technique can also be used as a way to validate the manufacture of columns.

(5) In cases where comparisons among different columns is of interest (e.g., were the columns manufactured the same, etc.), the relative binding capacities of different columns (of the same type or different types) can be compared by calculating the about 280 nm PQ values or by picking one column as a reference column to make the comparison, i.e, subtracting the PQ values of two columns at about 280 nm;

(6) In cases where it is of interest to pool the best fractions together for the next purification step, the PQ values can be used to decide which fractions are the best to pool together. The PQD values in these cases show not only the comparison of the protein of interest to contaminants, but also how much protein to add with respect to volume (for instance, would one want to add 5 mL to the pooled volume for an additional 2% of protein?).

Other embodiments are possible. For instance, a liquid chromatography run could go without collecting any liquid in tubes ("fractions") and an arbitrary fraction volume could instead be set where software could go along from start to finish and calculate relative areas of the arbitrary fraction volume. This arbitrary "fraction" can also be performed with respect to volume, time, or column volume.

Provided below is a description of an illustrative system upon which embodiments described herein may be implemented and utilized. Although some of the entities may be depicted as separate components, in some instances one or more of the components may be combined into a single device or location (and vice versa). Similarly, although certain functionality may be described as being performed by a single entity or component within the system, the functionality may, in some instances, be performed by multiple components or entities (and vice versa). Communication between entities and components may comprise the exchange of data or information using electronic messages on any suitable electronic communication medium as described below.

Figure 7:
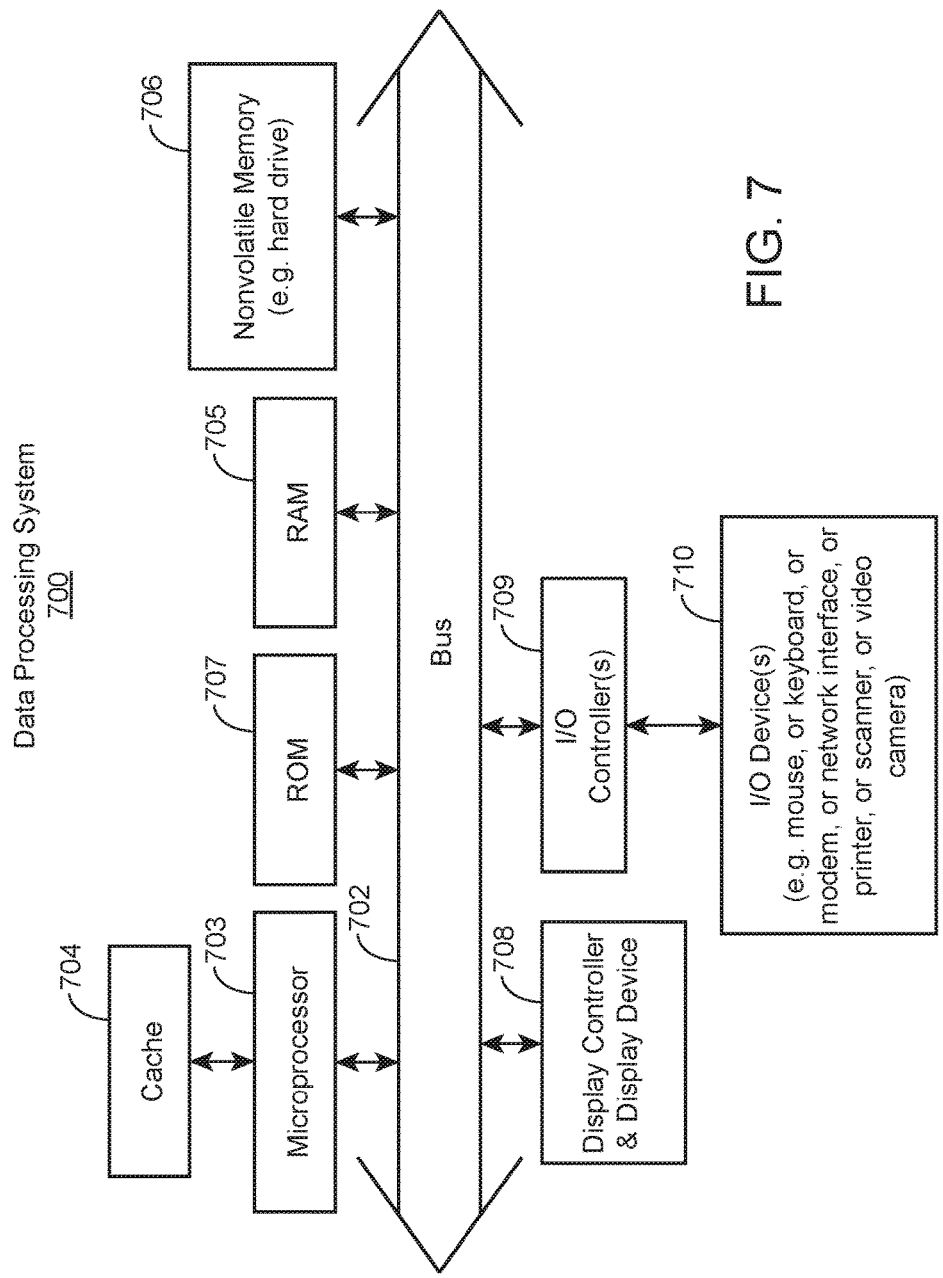
FIG. 7 depicts an example block diagram of a data processing system upon which the disclosed embodiments may be implemented.

FIG. 7 depicts an example block diagram of a data processing system upon which the disclosed embodiments may be implemented. Embodiments of the present invention may be practiced with various computer system configurations such as hand-held devices, microprocessor systems, microprocessor-based or programmable user electronics, minicomputers, mainframe computers and the like. The embodiments can also be practiced in distributed computing environments where tasks are performed by remote processing devices that are linked through a wire-based or wireless network. FIG. 7 shows one example of a data processing system, such as data processing system 700, which may be used with the present described embodiments. Note that while FIG. 7 illustrates various components of a data processing system, it is not intended to represent any particular architecture or manner of interconnecting the components as such details are not germane to the techniques described herein. It will also be appreciated that network computers and other data processing systems which have fewer components or perhaps more components may also be used. The data processing system of FIG. 7 may, for example, a personal computer (PC), workstation, tablet, smartphone or other hand-held wireless device, or any device having similar functionality.

As shown, the data processing system 701 includes a system bus 702 which is coupled to a microprocessor 703, a Read-Only Memory (ROM) 707, a volatile Random Access Memory (RAM) 705, as well as other nonvolatile memory 706. In the illustrated embodiment, microprocessor 703 is coupled to cache memory 704. System bus 702 can be adapted to interconnect these various components together and also interconnect components 703, 707, 705, and 706 to a display controller and display device 708, and to peripheral devices such as input/output ("I/O") devices 710. Types of I/O devices can include keyboards, modems, network interfaces, printers, scanners, video cameras, or other devices well known in the art. Typically, I/O devices 710 are coupled to the system bus 702 through I/O controllers 709. In one embodiment the I/O controller 709 includes a Universal Serial Bus ("USB") adapter for controlling USB peripherals or other type of bus adapter.

RAM 705 can be implemented as dynamic RAM ("DRAM") which requires power continually in order to refresh or maintain the data in the memory. The other nonvolatile memory 706 can be a magnetic hard drive, magnetic optical drive, optical drive, DVD RAM, or other type of memory system that maintains data after power is removed from the system. While FIG. 7 shows that nonvolatile memory 706 as a local device coupled with the rest of the components in the data processing system, it will be appreciated by skilled artisans that the described techniques may use a nonvolatile memory remote from the system, such as a network storage device coupled with the data processing system through a network interface such as a modem or Ethernet interface (not shown).

With these embodiments in mind, it will be apparent from this description that aspects of the described techniques may be embodied, at least in part, in software, hardware, firmware, or any combination thereof. For example, a computer apparatus or data processing system may comprise a processor and a memory coupled with the processor, the memory adapted to store instructions to be executed by the processor for analyzing liquid chromatograph data as described herein. It should also be understood that embodiments can employ various computer-implemented functions involving data stored in a data processing system. That is, the techniques may be carried out in a computer or other data processing system in response executing sequences of instructions stored in memory. In various embodiments, hardwired circuitry may be used independently, or in combination with software instructions, to implement these techniques. For instance, the described functionality may be performed by specific hardware components containing hardwired logic for performing operations, or by any combination of custom hardware components and programmed computer components. The techniques described herein are not limited to any specific combination of hardware circuitry and software.

Embodiments herein may also be in the form of computer code stored on a computer-readable medium. Computer-readable media can also be adapted to store computer instructions, which when executed by a computer or other data processing system, such as data processing system 700, are adapted to cause the system to perform operations according to the techniques described herein. Computer-readable media can include any mechanism that stores information in a form accessible by a data processing device such as a computer, network device, tablet, smartphone, or any device having similar functionality. Examples of computer-readable media include any type of tangible article of manufacture capable of storing information thereon such as a hard drive, floppy disk, DVD, CD-ROM, magnetic-optical disk, ROM, RAM, EPROM, EEPROM, flash memory and equivalents thereto, a magnetic or optical card, or any type of media suitable for storing electronic data. Computer-readable media can also be distributed over a network-coupled computer system, which can be stored or executed in a distributed fashion.

Throughout the foregoing description, for the purposes of explanation, numerous specific details were set forth in order to provide a thorough understanding of the invention. It will be apparent, however, to persons skilled in the art that these embodiments may be practiced without some of these specific details. Accordingly, the scope and spirit of the invention should be judged in terms of the claims which follow as well as the legal equivalents thereof.

What is claimed is:

1. A method of separating components of a mixture, the method comprising:
    performing a first run of a liquid chromatography process on the mixture through a first liquid chromatography column;
    collecting, by a data processing system, first volume fractions data from the first liquid chromatography column for a first absorbance wavelength of light $\lambda 1$ from the first run of a liquid chromatography process on the mixture, wherein the first liquid chromatography column screens for a first characteristic of the mixture;
    obtaining a first set of purity quotient values PQ1 by normalizing a first relative peak area for a first volume of a component of interest in the mixture for the first absorbance wavelength $\lambda 1$;
    performing a second run of the liquid chromatography process on the mixture through a second liquid chromatography column;
    collecting, by the data processing system, second volume fractions data from the second liquid chromatography column for a second absorbance wavelength of light $\lambda 2$ from the second run of a liquid chromatography process on the mixture, wherein the second liquid chromatography column screens for a second characteristic of the mixture;
    obtaining a second set of purity quotient values PQ2 by normalizing a second relative peak area for a second volume of the component of interest in the mixture for the second absorbance wavelength $\lambda 2$;
    storing the values PQ1 and PQ2 in a memory;
    obtaining a first set of purity quotient difference ("PQD") values by calculating, by the data processing system, a difference between values PQ1 and PQ2 for each volume fraction location of the first and second volumes to obtain a respective PQD value for each volume fraction;
    displaying in a graphical display the first set of PQD values;
    selecting volume fractions to pool together based on the display of the first set of PQD values, wherein selecting the volume fractions to pool together comprises selecting only volume fractions having PQD values greater than zero; and
    pooling the selected volume fractions together.

2. The method of claim 1, wherein the first and second liquid chromatography runs are the same liquid chromatography run, wherein the component of interest absorbs at both wavelengths $\lambda 1$ and $\lambda 2$, and wherein the difference between values PQ1 and PQ2 is calculated by subtracting the values PQ1 at wavelength $\lambda 1$ from the values PQ2 at wavelength $\lambda 2$.

3. The method of claim 1, wherein the first and second liquid chromatography runs are the same liquid chromatography run, wherein the component of interest absorbs at wavelength $\lambda 1$ and a known contaminant absorbs at wavelength $\lambda 2$, and wherein the difference between values PQ1 and PQ2 is calculated by subtracting the values PQ2 at wavelength $\lambda 2$ from the values PQ1 at wavelength $\lambda 1$.

4. The method of claim 1, wherein the first and second liquid chromatography runs are the same liquid chromatography run, wherein the component of interest absorbs at wavelength $\lambda 1$ and also binds with DNA that absorbs at wavelength $\lambda 2$, and wherein the values PQ1 at wavelength $\lambda 1$ are subtracted from the values PQ2 at wavelength $\lambda 2$ to identify locations where there is maximum overlap between DNA and protein.

5. The method of claim 1, wherein the first and second liquid chromatography runs are different runs and the wavelengths $\lambda 1$ and $\lambda 2$ are the same wavelength for both of the different runs, and wherein the component of interest absorbs at that wavelength.

6. The method of claim 5, wherein the first and second columns are the same column and a performance of the column between runs is determined by subtracting the values PQ1 from PQ2.

7. The method of claim 5, wherein the first and second columns are different columns and a comparative performance of the first and second columns is determined by subtracting the values PQ1 from PQ2.

8. The method of claim 1 further comprising:
    collecting, by the data processing system, third volume fractions data from a third liquid chromatography column for the two absorbance wavelengths $\lambda 1$ and $\lambda 2$ from the third run of the liquid chromatography process on the mixture, wherein the third liquid chromatography column screens for a second characteristic of the mixture different from the first characteristic, and wherein one variable of the liquid chromatography process is varied in the third run;
    normalizing a third relative peak area for a third volume of the component of interest in the mixture for the first absorbance wavelength $\lambda 1$ to obtain a third set of purity quotient values PQ3;
    normalizing a fourth relative peak area for a fourth volume of the component of interest in the mixture for the second absorbance wavelength $\lambda 2$ to obtain a fourth set of purity quotient values PQ4;
    storing the values PQ3 and PQ4 in the memory;
    calculating, by the data processing system, a difference between PQ3 and PQ4 for each volume fraction location to obtain a second set of PQD values;
    displaying in a graphical display the first and second sets of PQD values for the first and second runs of the liquid chromatography process superimposed on each other for each volume fraction location; and
    determining which of the first or second sets of PQD values indicates better separation the component of interest from components other than the component of interest in the mixture based on the first and second sets of PQD values.

9. The method of claim 8 wherein a two-dimensional representation of the first and second sets of PQD values is displayed.

10. The method of claim 1, wherein normalizing the first relative peak area comprises dividing the first relative peak area of the component of interest by a total collected volume of the component of interest in the mixture at each volume fraction location of the first volume.

11. The method of claim 1 further comprising:
performing three or more runs of the liquid chromatography process on the mixture, wherein one variable of the liquid chromatography process is varied for each additional run of the process; and
displaying a representation of PQD values in three or more dimensions based on the three or more runs of the liquid chromatography process respectively.

12. The method of claim 1, wherein multiple runs of the liquid chromatography process are compared to determine how to optimally set one or more variables of the process.

13. The method of claim 12, wherein setting the one or more variables comprises setting one or more variables selected from the group of variables consisting of column type, pH of the mobile phase liquid, conductivity of the mobile phase liquid, and flow rate of the mobile phase liquid.

14. The method of claim 1 wherein the liquid chromatography process is operable to be applied to any absorbance wavelength that can be measured by a spectrophotometric detector.

15. The method of claim 1 wherein normalizing of the first and second relative peak areas for the first and second volumes comprises normalizing with respect to total volume of the component of interest in the mixture.

16. The method of claim 1 wherein normalizing of the first and second relative peak areas for the first and second volumes comprises normalizing with respect to column volume.

17. The method of claim 1 wherein normalizing of the first and second relative peak areas for the first and second volumes comprises normalizing with respect to time.

18. The method of claim 1 wherein the component of interest in the mixture uniquely absorbs light at a particular wavelength.

19. A system for separating components of a mixture, the system comprising:
a processor;
a memory coupled with the processor, wherein the memory is adapted to store liquid chromatography data and instructions to be executed by the processor for analyzing the liquid chromatography data, the instructions, when executed by the processor, causing the system to:
perform a first run of a liquid chromatography process on the mixture through a first liquid chromatography column;
collect first volume fractions data from the first liquid chromatography column for a first absorbance wavelength of light $\lambda 1$ from the first run of a liquid chromatography process on the mixture, wherein the first liquid chromatography column screens for a first characteristic of the mixture;
obtain a first set of purity quotient values PQ1 by normalizing a first relative peak area for a first volume of a component of interest in the mixture for the first absorbance wavelength $\lambda 1$;
perform a second run of a liquid chromatography process on the mixture through a second liquid chromatography column;
collect second volume fractions data from the second liquid chromatography column for a second absorbance wavelength of light $\lambda 2$ from the second run of a liquid chromatography process on the mixture, wherein the second liquid chromatography column screens for a second characteristic of the mixture;
obtain a second set of purity quotient values PQ2 by normalizing a second relative peak area for the second volume of the component of interest in the mixture for the second absorbance wavelength $\lambda 2$;
store the values PQ1 and PQ2 in the memory;
obtain a first set of purity quotient difference values ("PQD") by calculating, by the processor, a difference between values PQ1 and PQ2 for each volume fraction location of the first and second volumes to obtain a respective PQD value for each volume fraction;
display in a graphical display the first set of PQD values; and
select volume fractions to pool together based on the display of the first set of PQD values, wherein the volume fractions to pool together are selected only from volume fractions having PQD values greater than zero.

20. The system of claim 19, wherein the first and second liquid chromatography runs are the same liquid chromatography run, wherein the component of interest absorbs at both wavelengths $\lambda 1$ and $\lambda 2$, and wherein the component of interest is separated from impurities that also absorb at wavelength $\lambda 2$ by subtracting the values PQ1 at wavelength $\lambda 1$ from the values PQ2 at wavelength $\lambda 2$.

* * * * *